(12) United States Patent
Chavarria et al.

(10) Patent No.: US 10,159,500 B2
(45) Date of Patent: Dec. 25, 2018

(54) OSCILLATING RASP FOR USE IN AN ORTHOPAEDIC SURGICAL PROCEDURE

(71) Applicant: DePuy Synthes Products, Inc., Raynham, MA (US)

(72) Inventors: Jason M. Chavarria, Warsaw, IN (US); Matthew T. Stone, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/862,436

(22) Filed: Jan. 4, 2018

(65) Prior Publication Data

US 2018/0125508 A1 May 10, 2018

Related U.S. Application Data

(60) Division of application No. 14/809,303, filed on Jul. 27, 2015, now Pat. No. 9,861,376, which is a continuation of application No. 13/940,540, filed on Jul. 12, 2013, now Pat. No. 9,089,348, which is a (Continued)

(51) Int. Cl.
*A61B 17/16* (2006.01)

(52) U.S. Cl.
CPC ...... *A61B 17/1684* (2013.01); *A61B 17/1659* (2013.01)

(58) Field of Classification Search
CPC ............ A61B 17/1659; A61B 17/1666; A61B 17/1684; A61F 2/40; A61F 2/4081
USPC .......... 606/79–81, 84–87, 96, 167, 170–172, 606/176–178; 623/19.11–19.3; 407/29.1–29.14; 30/340, 342, 392–394
See application file for complete search history.

(56) References Cited

U.S. PATENT DOCUMENTS

| 166,868 | A | * | 8/1875 | Haptonstall | ............ | B23D 71/00 |
| | | | | | | 407/29.14 |
| 472,259 | A | * | 4/1892 | Goodell | .................. | A43D 5/10 |
| | | | | | | 12/104.5 |

(Continued)

FOREIGN PATENT DOCUMENTS

| EP | 0378002 B1 | 12/1993 |
| EP | 0903127 A2 | 3/1999 |

(Continued)

OTHER PUBLICATIONS

Australian Patent Examination Report No. 1 issued by the Australian Patent Office, dated Oct. 2, 2014, 5 pages.

(Continued)

*Primary Examiner* — Eric S Gibson
(74) *Attorney, Agent, or Firm* — Barnes & Thornburg LLP

(57) ABSTRACT

An oscillating surgical rasp for use in the surgical preparation of a glenoid of a patient prior to implantation of an augmented glenoid prosthesis comprises an attachment head and a cutting head secured to the attachment head. The attachment head has a body that extends along a longitudinal axis from a first end configured to be secured in a chuck of an oscillating tool to a second end secured to the cutting head. The first end of the body of the attachment head defines an axis of oscillation that extends orthogonal to the longitudinal axis of the oscillating surgical rasp. Surgical methods for the use of such oscillating rasps are also disclosed.

10 Claims, 10 Drawing Sheets

Related U.S. Application Data division of application No. 13/016,404, filed on Jan. 28, 2011, now Pat. No. 8,486,076.

(56) References Cited

U.S. PATENT DOCUMENTS

| | | | | |
|---|---|---|---|---|
| 1,032,897 | A * | 7/1912 | Hamilton | B23D 71/00 407/29.1 |
| 1,042,728 | A * | 10/1912 | Vernaz | B23D 71/00 407/29.14 |
| 2,698,621 | A * | 1/1955 | Fernandez | A61B 17/1695 30/374 |
| 2,770,037 | A * | 11/1956 | Bjorklund | A61F 15/02 30/272.1 |
| 3,630,204 | A * | 12/1971 | Fishbein | A61B 17/1666 408/224 |
| 3,913,585 | A * | 10/1975 | Wolvek | A61B 17/32 30/277 |
| 4,023,572 | A * | 5/1977 | Weigand | A61B 17/1666 30/276 |
| 4,178,663 | A * | 12/1979 | Hayes | B23D 71/04 407/29.15 |
| RE30,794 | E * | 11/1981 | Hayes | B23D 71/04 407/29.15 |
| 4,625,725 | A * | 12/1986 | Davison | A61B 17/1659 407/29.1 |
| 4,865,605 | A | 9/1989 | Dines et al. | |
| 5,122,142 | A * | 6/1992 | Pascaloff | A61B 17/144 606/171 |
| 5,169,401 | A | 12/1992 | Lester et al. | |
| 5,261,915 | A * | 11/1993 | Durlacher | A61B 17/1659 606/53 |
| 5,282,865 | A | 2/1994 | Dong | |
| 5,306,285 | A * | 4/1994 | Miller | B23D 61/006 30/355 |
| 5,342,365 | A * | 8/1994 | Waldman | A61B 17/1659 407/29.1 |
| 5,342,635 | A | 8/1994 | Waldman | |
| 5,370,704 | A | 12/1994 | Decarlo | |
| 5,382,249 | A * | 1/1995 | Fletcher | B23D 51/10 606/176 |
| 5,403,318 | A * | 4/1995 | Boehringer | B23D 59/04 606/178 |
| 5,409,491 | A * | 4/1995 | Boehringer | B23D 59/04 606/178 |
| 5,489,310 | A * | 2/1996 | Mikhail | A61B 17/1684 623/19.11 |
| 5,540,693 | A * | 7/1996 | Fisher | A61B 17/1659 606/79 |
| 5,553,476 | A | 9/1996 | Oehy et al. | |
| 5,593,448 | A * | 1/1997 | Dong | A61F 2/4081 606/86 R |
| 5,913,867 | A | 6/1999 | Dion | |
| 5,919,195 | A * | 7/1999 | Wilson | A61B 17/1666 606/80 |
| 6,022,353 | A | 2/2000 | Fletcher et al. | |
| 6,245,074 | B1 | 6/2001 | Allard et al. | |
| 6,358,251 | B1 * | 3/2002 | Mirza | A61B 17/1617 606/172 |
| 6,364,910 | B1 * | 4/2002 | Shultz | A61B 17/1659 606/86 R |
| 6,379,386 | B1 * | 4/2002 | Resch | A61B 17/1604 623/19.13 |
| 6,436,101 | B1 * | 8/2002 | Hamada | A61B 17/1604 606/85 |
| 6,503,253 | B1 | 1/2003 | Fletcher et al. | |
| 6,589,281 | B2 * | 7/2003 | Hyde, Jr. | A61B 17/1604 623/18.11 |
| 6,663,636 | B1 * | 12/2003 | Lin | A61B 17/1659 606/79 |
| 6,673,115 | B2 * | 1/2004 | Resch | A61B 17/1604 606/79 |
| 6,699,289 | B2 * | 3/2004 | Iannotti | A61B 17/1684 623/19.11 |
| 6,723,101 | B2 | 4/2004 | Fletcher et al. | |
| 6,746,451 | B2 * | 6/2004 | Middleton | A61B 17/1617 606/180 |
| 6,780,190 | B2 | 8/2004 | Maroney | |
| 6,783,548 | B2 * | 8/2004 | Hyde, Jr. | A61B 17/1604 623/18.12 |
| 6,884,246 | B1 * | 4/2005 | Sonnabend | A61B 17/1617 606/80 |
| 6,911,047 | B2 * | 6/2005 | Rockwood, Jr. | A61F 2/4081 128/898 |
| 7,108,698 | B2 * | 9/2006 | Robbins | A61B 17/025 600/210 |
| 7,160,306 | B2 * | 1/2007 | Matsuzaki | A61B 17/1604 606/86 R |
| 7,160,328 | B2 * | 1/2007 | Rockwood, Jr. | A61F 2/4081 128/898 |
| 7,220,264 | B1 | 5/2007 | Hershberger | |
| 7,326,215 | B2 * | 2/2008 | Myers | A61B 17/1624 606/80 |
| 7,329,284 | B2 | 2/2008 | Maroney et al. | |
| 7,371,240 | B2 * | 5/2008 | Pinczewski | A61B 17/154 128/898 |
| 7,473,254 | B2 * | 1/2009 | White | A61B 17/1617 606/81 |
| 7,527,628 | B2 * | 5/2009 | Fletcher | B23D 51/10 606/177 |
| 7,572,259 | B2 | 8/2009 | Desarzens et al. | |
| 7,611,516 | B2 | 11/2009 | Maroney | |
| 7,621,915 | B2 | 11/2009 | Frederick et al. | |
| 7,632,273 | B2 * | 12/2009 | Schnieders | A61B 17/1659 606/79 |
| 7,670,343 | B2 * | 3/2010 | Meridew | A61B 17/1666 606/81 |
| 7,744,616 | B2 * | 6/2010 | O'Donoghue | A61B 17/142 606/177 |
| 7,753,959 | B2 * | 7/2010 | Berelsman | A61F 2/4081 623/19.11 |
| 7,806,898 | B2 * | 10/2010 | Justin | A61B 17/1675 606/85 |
| 7,867,236 | B2 * | 1/2011 | Hodorek | A61B 17/1659 606/84 |
| 7,892,287 | B2 * | 2/2011 | Deffenbaugh | A61F 2/4081 623/19.11 |
| 7,901,424 | B2 * | 3/2011 | Fletcher | B23D 51/10 606/176 |
| 7,909,828 | B2 | 3/2011 | Fehlbaum et al. | |
| 7,927,335 | B2 * | 4/2011 | Deffenbaugh | A61B 17/1617 606/87 |
| 7,955,337 | B2 * | 6/2011 | Lee | A61B 17/1659 606/85 |
| 8,052,689 | B2 | 11/2011 | Sherry et al. | |
| 8,133,234 | B2 * | 3/2012 | Meridew | A61F 2/4609 606/91 |
| 8,216,262 | B2 * | 7/2012 | O'Donoghue | A61B 17/142 606/178 |
| 8,241,289 | B2 * | 8/2012 | Maisonneuve | A61B 17/164 606/80 |
| 8,246,621 | B2 * | 8/2012 | Poncet | A61B 17/1778 606/79 |
| 8,277,452 | B2 * | 10/2012 | Graves | A61B 17/1617 606/79 |
| 8,425,614 | B2 * | 4/2013 | Winslow | A61F 2/4003 623/19.11 |
| 8,486,076 | B2 * | 7/2013 | Chavarria | A61B 17/1659 606/85 |
| 8,506,569 | B2 * | 8/2013 | Keefer | A61B 17/1659 606/85 |
| 8,523,867 | B2 * | 9/2013 | Rauscher | A61B 17/1684 606/180 |
| 8,556,901 | B2 * | 10/2013 | Anthony | A61B 17/1659 606/85 |
| 8,603,180 | B2 * | 12/2013 | White | A61B 17/1617 606/91 |
| 9,089,348 | B2 * | 7/2015 | Chavarria | A61B 17/1659 |
| 9,861,376 | B2 | 1/2018 | Chavarria et al. | |

(56) References Cited

U.S. PATENT DOCUMENTS

| | | | |
|---|---|---|---|
| 2002/0095214 A1* | 7/2002 | Hyde, Jr. | A61B 17/1604 623/18.12 |
| 2002/0099381 A1 | 7/2002 | Maroney | |
| 2002/0099445 A1 | 7/2002 | Maroney et al. | |
| 2002/0116023 A1* | 8/2002 | Fletcher | B23D 51/10 606/176 |
| 2002/0138148 A1* | 9/2002 | Hyde, Jr. | A61B 17/1604 623/18.11 |
| 2003/0014067 A1* | 1/2003 | Kullmer | B23D 61/006 606/176 |
| 2004/0034431 A1 | 2/2004 | Maroney et al. | |
| 2004/0243134 A1 | 12/2004 | Walker et al. | |
| 2005/0015153 A1* | 1/2005 | Goble | A61F 2/3859 623/23.46 |
| 2005/0021038 A1 | 1/2005 | Maroney | |
| 2005/0043805 A1* | 2/2005 | Chudik | A61B 17/1684 623/19.14 |
| 2005/0148843 A1* | 7/2005 | Roose | A61B 17/17 600/407 |
| 2005/0192583 A1 | 9/2005 | Walker et al. | |
| 2005/0192584 A1 | 9/2005 | Walker et al. | |
| 2005/0209700 A1* | 9/2005 | Rockwood, Jr. | A61F 2/4081 623/19.12 |
| 2005/0234463 A1 | 10/2005 | Hershberger et al. | |
| 2005/0288676 A1* | 12/2005 | Schnieders | A61B 17/1659 606/79 |
| 2006/0009774 A1* | 1/2006 | Goble | A61B 17/157 606/85 |
| 2006/0009776 A1* | 1/2006 | Justin | A61B 17/1675 606/87 |
| 2006/0009854 A1* | 1/2006 | Justin | A61B 17/1675 623/20.15 |
| 2006/0058804 A1* | 3/2006 | Mollstam | A61M 5/14232 606/80 |
| 2006/0069444 A1* | 3/2006 | Deffenbaugh | A61F 2/30734 623/19.11 |
| 2006/0074430 A1 | 4/2006 | Deffenbaugh et al. | |
| 2006/0079963 A1* | 4/2006 | Hansen | A61F 2/40 623/19.11 |
| 2006/0142774 A1* | 6/2006 | Metzger | A61B 17/155 606/79 |
| 2006/0142865 A1* | 6/2006 | Hyde, Jr. | A61B 17/1604 623/18.12 |
| 2006/0195194 A1* | 8/2006 | Gunther | A61B 17/15 623/19.13 |
| 2006/0229627 A1* | 10/2006 | Hunt | A61B 17/1659 606/86 R |
| 2007/0016304 A1* | 1/2007 | Chudik | A61B 17/1684 623/19.11 |
| 2007/0038302 A1* | 2/2007 | Shultz | A61B 17/1684 623/19.11 |
| 2007/0092841 A1 | 4/2007 | Kawashima | |
| 2007/0198002 A1 | 8/2007 | Melsheimer et al. | |
| 2007/0219637 A1* | 9/2007 | Berelsman | A61F 2/4081 623/19.11 |
| 2007/0219638 A1* | 9/2007 | Jones | A61F 2/4081 623/19.11 |
| 2007/0233131 A1 | 10/2007 | Song et al. | |
| 2007/0293868 A1 | 12/2007 | Delfosse et al. | |
| 2008/0003066 A1* | 1/2008 | Haugaard | B23D 71/04 407/29.1 |
| 2008/0038302 A1 | 2/2008 | Tanaka | |
| 2008/0147070 A1* | 6/2008 | Michel | A61B 17/1624 606/80 |
| 2008/0147075 A1 | 6/2008 | Bonutti | |
| 2008/0183297 A1* | 7/2008 | Boileau | A61B 17/1635 623/19.14 |
| 2008/0275453 A1 | 11/2008 | Lafosse et al. | |
| 2009/0093815 A1 | 4/2009 | Fletcher et al. | |
| 2009/0163921 A1* | 6/2009 | Lechot | A61B 17/1617 606/81 |
| 2009/0270993 A1* | 10/2009 | Maisonneuve | A61B 17/1684 623/19.14 |
| 2009/0312779 A1* | 12/2009 | Boykin | B27B 5/32 606/171 |
| 2010/0191246 A1* | 7/2010 | Howald | A61F 2/34 606/91 |
| 2010/0241235 A1* | 9/2010 | Basamania | A61F 2/4081 623/19.11 |
| 2010/0249938 A1* | 9/2010 | Gunther | A61B 17/15 623/19.11 |
| 2010/0268238 A1 | 10/2010 | Sikora et al. | |
| 2010/0298834 A1* | 11/2010 | Hildebrandt | A61B 17/025 606/80 |
| 2011/0028977 A1* | 2/2011 | Rauscher | A61B 17/1684 606/80 |
| 2011/0029088 A1* | 2/2011 | Rauscher | A61B 17/1778 623/19.11 |
| 2011/0213371 A1* | 9/2011 | Anthony | A61B 17/1659 606/85 |
| 2011/0213372 A1* | 9/2011 | Keefer | A61B 17/1659 606/85 |
| 2011/0213427 A1* | 9/2011 | Fitz | A61B 17/154 606/86 R |
| 2011/0213428 A1* | 9/2011 | Fitz | A61B 17/154 606/86 R |
| 2011/0213429 A1* | 9/2011 | Lang | A61B 17/154 606/86 R |
| 2011/0213430 A1* | 9/2011 | Lang | A61B 17/154 606/86 R |
| 2011/0213431 A1* | 9/2011 | Fitz | A61B 17/154 606/86 R |
| 2012/0109226 A1* | 5/2012 | Iannotti | A61B 17/88 606/86 R |
| 2012/0143267 A1* | 6/2012 | Iannotti | A61B 17/1746 606/86 R |
| 2012/0197258 A1* | 8/2012 | Chavarria | A61B 17/1659 606/85 |
| 2012/0226283 A1* | 9/2012 | Meridew | A61B 17/1659 606/81 |
| 2012/0239051 A1* | 9/2012 | De Wilde | A61F 2/4081 606/96 |
| 2012/0239156 A1* | 9/2012 | De Wilde | A61F 2/4081 623/19.11 |
| 2013/0072940 A1* | 3/2013 | Dawood | A61B 17/1746 606/91 |
| 2013/0245631 A1* | 9/2013 | Bettenga | A61B 17/1666 606/91 |
| 2013/0296867 A1* | 11/2013 | Chavarria | A61B 17/1659 606/80 |
| 2013/0296870 A1* | 11/2013 | Keefer | A61B 17/1659 606/85 |
| 2013/0345817 A1* | 12/2013 | Long | A61B 17/15 623/19.14 |
| 2014/0012266 A1* | 1/2014 | Bonin, Jr. | A61B 17/15 606/88 |
| 2014/0039505 A1* | 2/2014 | Anthony | A61B 17/1659 606/81 |
| 2014/0081342 A1* | 3/2014 | Iannotti | A61B 17/88 606/86 R |

FOREIGN PATENT DOCUMENTS

| | | |
|---|---|---|
| EP | 1224912 A2 | 7/2002 |
| EP | 1402853 A2 | 3/2004 |
| EP | 1550419 A2 | 7/2005 |
| EP | 1639949 A1 | 3/2006 |
| EP | 1764046 A2 | 3/2007 |
| JP | 2008528110 A | 7/2008 |
| WO | 2001034040 A1 | 5/2001 |
| WO | 2004108012 A2 | 12/2004 |
| WO | 2006/078864 A1 | 7/2006 |
| WO | 2006078511 A1 | 7/2006 |
| WO | WO 2006078864 A1 * 7/2006 ......... A61B 17/1675 | |
| WO | 2006136955 A1 | 12/2006 |
| WO | 2008005941 A2 | 1/2008 |

(56) References Cited

FOREIGN PATENT DOCUMENTS

| WO | 2009111639 A1 | 9/2009 |
|---|---|---|
| WO | 2010033473 A2 | 3/2010 |
| WO | 2011012317 A1 | 2/2011 |

OTHER PUBLICATIONS

Global AP Adjustable Prosthesis, Surgical Technique, Copyright 2009, 64 pages.
Delta Xtend Reverse Shoulder System, Design Rationale and Surgical Technique, Copyright 2009, 64 pages.
European Search Report, European Patent Application No. 12151782. 5-2310, dated May 7, 2012, 6 pages.
Extended European Search Report, European Patent Application No. 10196415.5-2310, dated Apr. 21, 2011, 7 pages.
Extended European Search Report, European Patent Application No. 10196412.0-2310, dated Apr. 20, 2011, 7 pages.
Australian Search Report, Australian Patent Application No. 2012200276, dated Sep. 3, 2013, 3 pages.
Japanese Search Report, Japanese Patent Application No. 2012-015026, dated Aug. 26, 2015, 4 pages.
Extended European Search Report, European Application No. 16160492. 1-1654, dated Jun. 2, 2016, 6 pages.
European Office Action, European Application No. 16160492.1-1664, dated Feb. 28, 2017, 4 pages.

\* cited by examiner

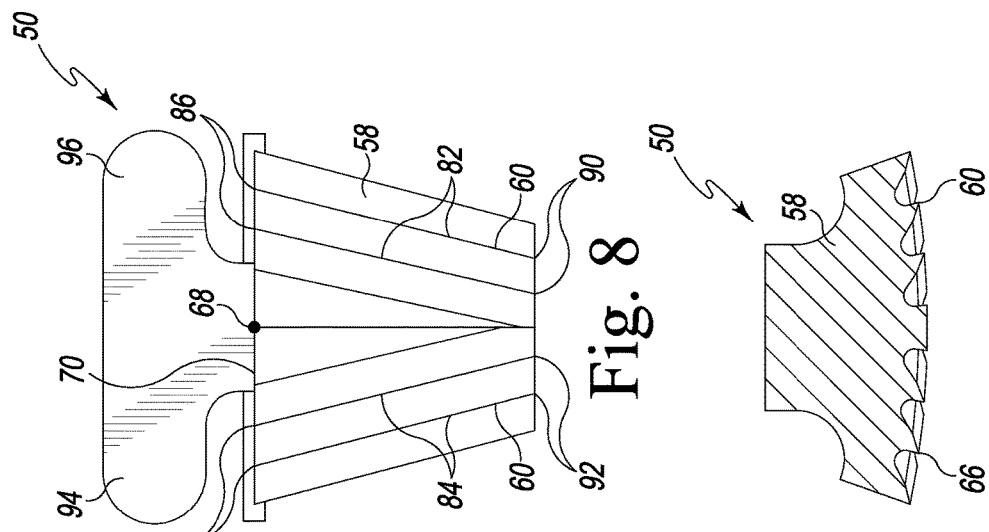
Fig. 8
Fig. 9
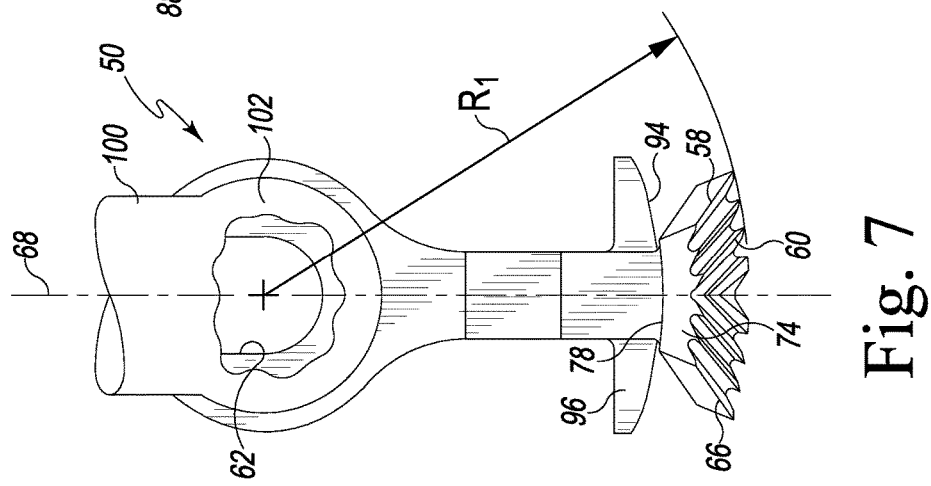
Fig. 7
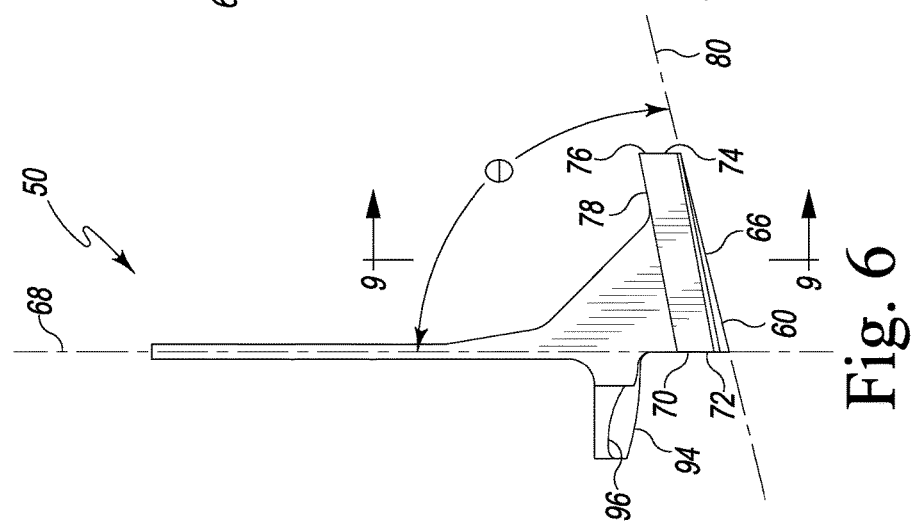
Fig. 6

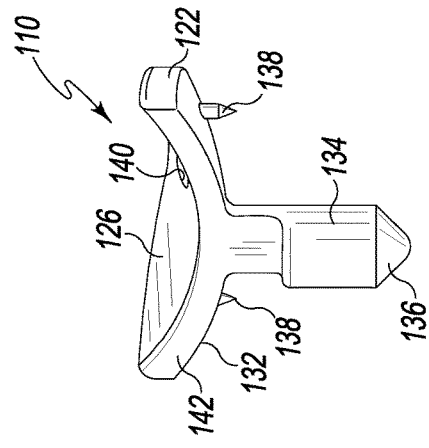
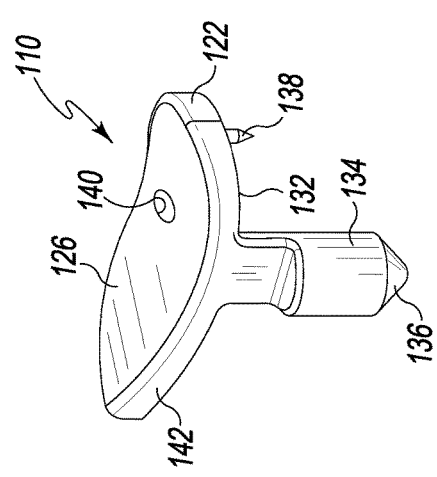
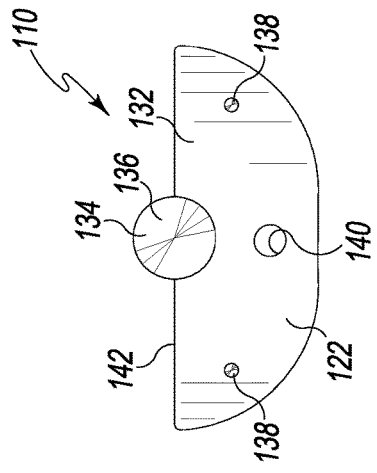
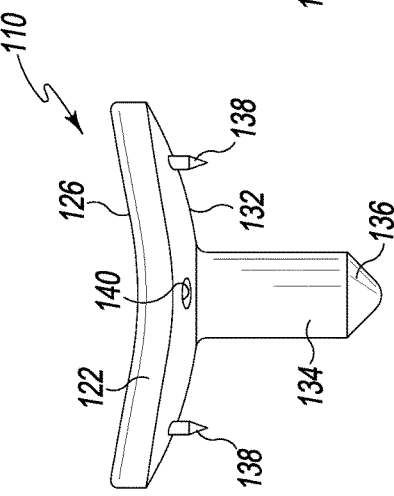
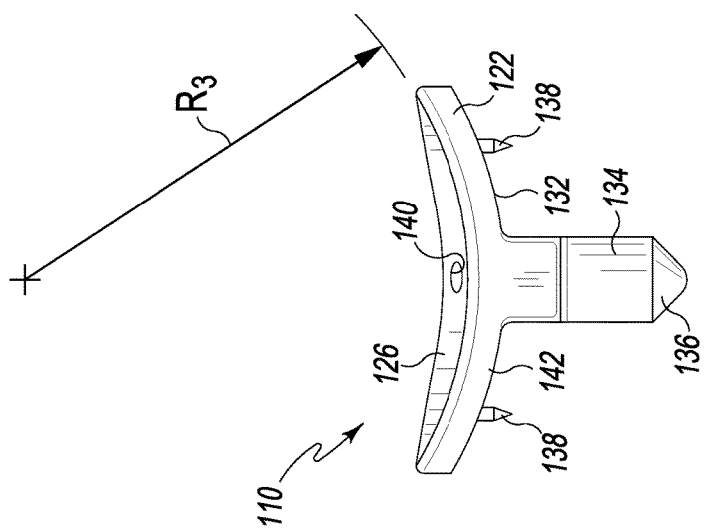

OSCILLATING RASP FOR USE IN AN ORTHOPAEDIC SURGICAL PROCEDURE

This application is a divisional application under 35 U.S.C. § 121 to U.S. patent application Ser. No. 14/809,303, which was filed on Jul. 27, 2015 and is a continuation application of U.S. patent application Ser. No. 13/940,540, now U.S. Pat. No. 9,089,348, which was filed on Jul. 12, 2013 and is a divisional application of U.S. patent application Ser. No. 13/016,404, now U.S. Pat. No. 8,486,076, which was filed on Jan. 28, 2011, the entirety of each of which is hereby incorporated by reference.

CROSS REFERENCE

Cross reference is made to U.S. patent application Ser. No. 12/956,914, now U.S. Pat. No. 8,506,569, which was filed on Nov. 30, 2010 and is entitled "Reciprocating Rasps for Use in an Orthopaedic Surgical Procedure" and to U.S. patent application Ser. No. 12/956,881, now U.S. Pat. No. 8,556,901, that was filed on Nov. 30, 2010 and is entitled "Reciprocating Rasps for Use in an Orthopaedic Surgical Procedure", both of which are assigned to the same assignee as the present application and hereby incorporated by reference.

TECHNICAL FIELD

The present disclosure relates generally to an orthopaedic instrument for use in the performance of an orthopaedic joint replacement procedure, and more particularly to an oscillating rasp for use in the performance of an orthopaedic joint replacement procedure.

BACKGROUND

During the lifetime of a patient, it may be necessary to perform a total shoulder replacement procedure on the patient as a result of, for example, disease or trauma. In a total shoulder replacement procedure, a humeral component having a prosthetic head is used to replace the natural head of the patient's humerus. The humeral component typically includes an elongated stem that is implanted into the intramedullary canal of the patient's humerus. In such a total shoulder replacement procedure, the natural glenoid surface of the scapula is resurfaced or otherwise replaced with a glenoid component that provides a bearing surface upon which the prosthetic head of the humeral component articulates.

As alluded to above, the need for a shoulder replacement procedure may be created by the presence of any one of a number of conditions. One such condition is the deterioration of the patient's scapula in the area proximate to the glenoid surface as a result of, for example, glenohumeral arthritis. In such a condition, the erosion of the patient's scapula is generally observed posteriorly on the glenoid surface. Such erosion of the scapula renders treatment difficult, if not impossible, with a conventional glenoid component. One way to treat such a condition is by the use of a modified glenoid component, known generally as an augmented glenoid component. An augmented glenoid component has a posterior edge that is thicker than the corresponding anterior edge.

Simple surgical instruments such as revolving spherical or circular reamers are generally used to prepare the glenoid surface during a glenoid surgical procedure. This is sufficient since traditional glenoid components (i.e., non-augmented glenoid components) typically have a uniform backside geometry that is either curved or flat, which makes glenoid preparation fairly straightforward. However, the use of glenoid components with complex backside geometries (e.g., augmented glenoid components) makes bone preparation more of a challenge. A surgeon is forced to use a combination of reamers, saws, and burrs in the performance of a free-hand technique that requires frequent interruptions for intraoperative assessment to implant these complex components.

SUMMARY

According to one aspect, an augmented glenoid component includes a buttress on the posterior side of the component. The augmented glenoid component also includes an anchor peg with fins and a number of stabilizing pegs.

According to another aspect, an oscillating rasp allows for the surgical preparation of the bone necessary for the implantation of an augmented glenoid component with such complex geometry.

In an illustrative embodiment, an oscillating surgical rasp for use in the surgical preparation of a glenoid of a patient prior to implantation of an augmented glenoid prosthesis. The oscillating surgical rasp includes an attachment head configured to be secured in a chuck of an oscillating tool. The oscillating surgical rasp also includes a cutting head secured to the attachment head. The cutting head includes a cutting surface extending posteriorly from the longitudinal axis of the surgical rasp. The cutting surface has a plurality of cutting teeth arranged in a geometry that, when oscillated along a predetermined path in contact with the glenoid of the patient, corresponds with the geometry of the augmented glenoid prosthesis.

The cutting head of the oscillating surgical rasp may also include a depth stop extending anteriorly from the longitudinal axis of the cutting plate.

In an embodiment, an imaginary line extends posteriorly from the longitudinal axis of the surgical rasp along an outer surface of each of the plurality of cutting teeth. The imaginary line intersects the longitudinal axis of the surgical rasp to define an angle of intersection therebetween. The angle of intersection is between 30°-90°. In a more specific embodiment, the angle of intersection is between 30°-89° to produce a rounded surface in the superior/inferior direction. In a more specific embodiment, the angle of intersection is approximately 75°. In the case of a rasp for use in implanting a vault-type revision glenoid component, the angle of intersection is between 20°-30°.

The plurality of cutting teeth of the cutting head may include a superior cutting tooth and an inferior cutting tooth that is positioned inferiorly relative to the superior cutting tooth. An anterior end of the superior cutting tooth is spaced apart from an anterior end of the inferior cutting tooth by a first distance. A posterior end of the superior cutting tooth is spaced apart from a superior end of the inferior cutting tooth by a second distance that is shorter than the first distance.

The plurality of cutting teeth of the cutting head may include a number of superior cutting teeth and a number of inferior cutting teeth that are positioned inferiorly relative to the number of superior cutting teeth. The superior cutting teeth are arranged parallel to one another and the inferior cutting teeth are arranged parallel to one another. The superior cutting teeth and the inferior cutting teeth extend posteriorly from the longitudinal axis of the surgical rasp at an angle relative to one another so as to converge toward one another.

In an embodiment, the plurality of cutting teeth of the cutting head may be arranged in a geometry that, when oscillated along a predetermined path in contact with the glenoid of the patient, corresponds with the geometry of a posterior buttress of the augmented glenoid prosthesis.

According to another aspect, an orthopaedic surgical instrument assembly for use in the surgical preparation of a glenoid of a patient prior to implantation of an augmented glenoid prosthesis includes an oscillating surgical rasp. The oscillating surgical rasp includes an attachment head configured to be secured in a chuck of an oscillating tool and a cutting head secured to attachment head. The cutting head may include a cutting surface extending posteriorly from the longitudinal axis of the oscillating surgical rasp. The cutting surface has a plurality of cutting teeth arranged in a geometry that, when oscillated along a predetermined path in contact with the glenoid of the patient, corresponds with the geometry of the augmented glenoid prosthesis. The orthopaedic surgical instrument assembly also includes a rasp guide having a guide surface configured to guide the oscillating surgical rasp during operation thereof and an anchor surface that is opposite the guide surface and configured to be secured to the glenoid of the patient.

The cutting head of the oscillating surgical rasp may further include a depth stop extending anteriorly from the longitudinal axis of the oscillating surgical rasp. The guide surface of the rasp guide is configured to guide depth stop of the cutting head of the oscillating surgical rasp during operation thereof.

In an embodiment, the anchor surface of the rasp guide includes an anchor peg extending perpendicularly therefrom. The anchor peg is configured to be received into a hole formed in the glenoid of the patient.

In an embodiment, the guide surface of the rasp guide is concave.

The anchor surface of the rasp guide may also include a number of pointed anchoring pins extending perpendicularly therefrom. The anchoring pins are configured to be driven into bone tissue of the glenoid of the patient.

In an embodiment, the plurality of cutting teeth of the cutting head are arranged in a geometry that, when oscillated along a predetermined path in contact with the glenoid of the patient, corresponds with the geometry of a posterior buttress of the augmented glenoid prosthesis.

According to another aspect, a method of surgically implanting a glenoid component into the glenoid of a patient includes securing a rasp guide into the glenoid of the patient, oscillating a surgical rasp over the rasp guide so as to abrade bone tissue to form a cavity shaped to receive the glenoid component, and implanting the glenoid component in the cavity.

The surgical rasp may include an attachment head having a cutting head secured thereto. The attachment head may be secured to an oscillating power tool and the power tool operated so as to oscillate the cutting head of the surgical rasp.

The surgical rasp may include a cutting head having a depth stop. The rasp guide may include a guide surface facing outwardly from the glenoid of the patient. The surgical rasp may be advanced toward the glenoid of the patient until the depth stop of the surgical rasp contacts the guide surface of the rasp guide.

In an embodiment, an anchor hole is drilled into the glenoid of the patient. The rasp guide may include an anchor peg that extends perpendicularly therefrom. The anchor peg of the rasp guide is inserted in the drilled anchor hole.

A guide pin may be inserted into the glenoid of the patient. A reamer may then be advanced over the guide pin. The glenoid of the patient may then be reamed to create a reamed surface prior to oscillating the surgical rasp over the rasp guide to form the cavity shaped to receive the glenoid component.

A cannulated drill may be advanced over the guide pin and an anchor hole drilled into the reamed surface of the glenoid of the patient. The anchor peg of the rasp guide is then inserted into in the drilled anchor hole.

The glenoid component may be embodied as an augmented glenoid component having a buttress. The surgical rasp may be oscillated so as to abrade bone tissue to form a cavity shaped to receive the buttress of such an augmented glenoid component.

BRIEF DESCRIPTION OF THE DRAWINGS

The detailed description particularly refers to the following figures, in which:

FIGS. 6 and 7 are elevation views of the oscillating rasp of FIGS. 4 and 5;

FIG. 8 is a plan view of the oscillating rasp of FIGS. 4 and 5;

FIG. 9 is a cross sectional view of the oscillating rasp of FIGS. 4 and 5, taken along the line 9-9 of FIG. 6, as viewed in the direction of the arrows;

FIGS. 10 and 11 are perspective views of a rasp guide for use along with the oscillating rasp of FIGS. 4 and 5 in a surgical procedure to implant the augmented glenoid component of FIGS. 1-3;

FIGS. 12 and 13 are elevation views of the rasp guide of FIGS. 10 and 11;

FIG. 14 is a bottom elevation view of the rasp guide of FIGS. 10 and 11;

DETAILED DESCRIPTION OF THE DRAWINGS

Figures 1, 2, 3:
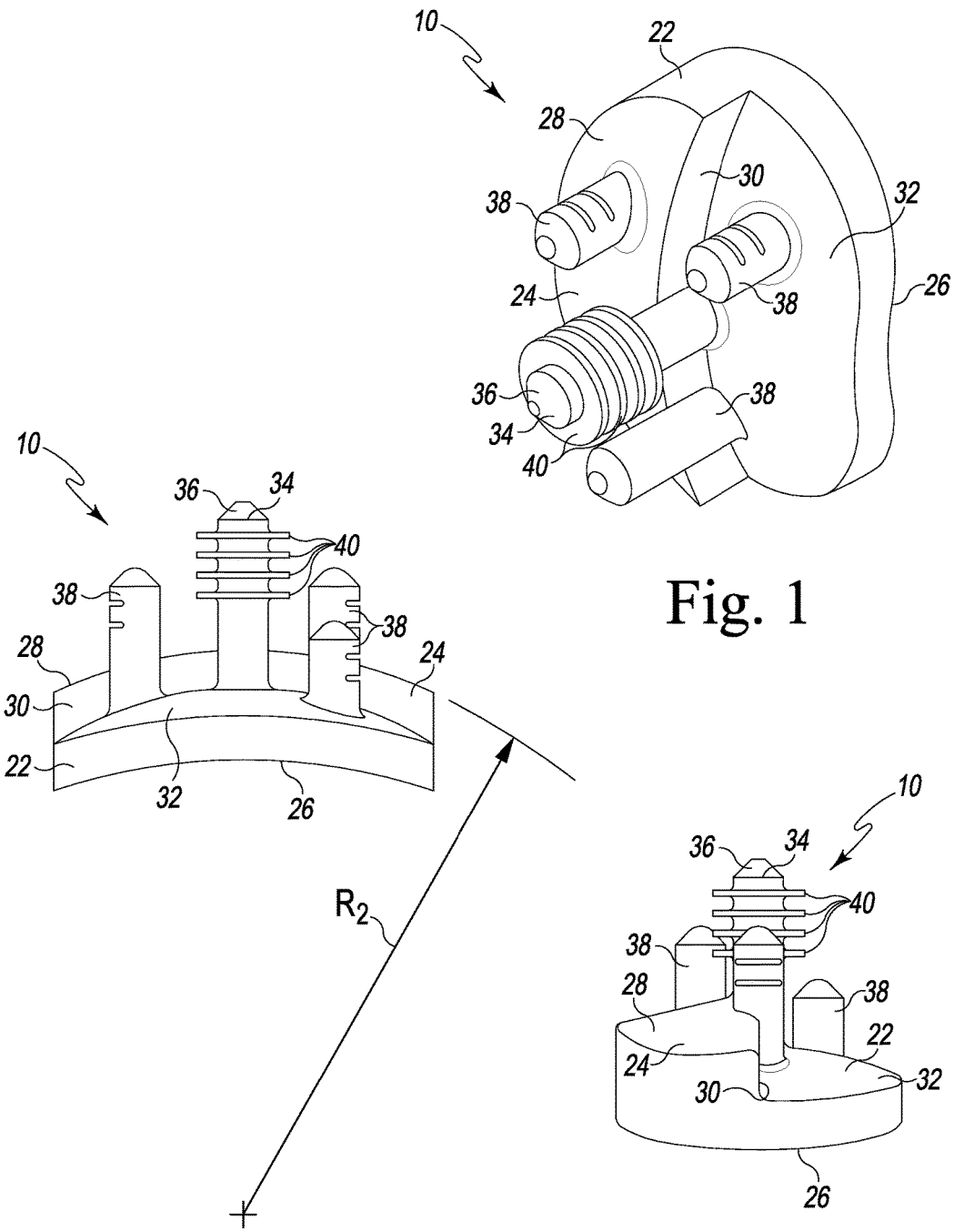
FIG. 1 is a perspective view of an augmented glenoid component.
FIGS. 2 and 3 are side elevation views of the augmented glenoid component of FIG. 1.
Figure 5:
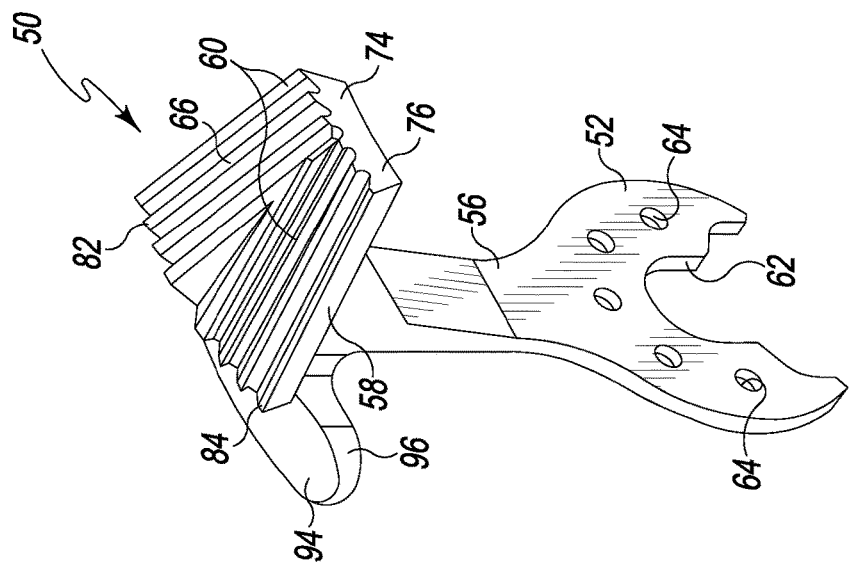
FIGS. 4 and 5 are perspective views of an oscillating rasp for use in a surgical procedure to implant the augmented glenoid component of FIGS. 1-3.
Figure 4:
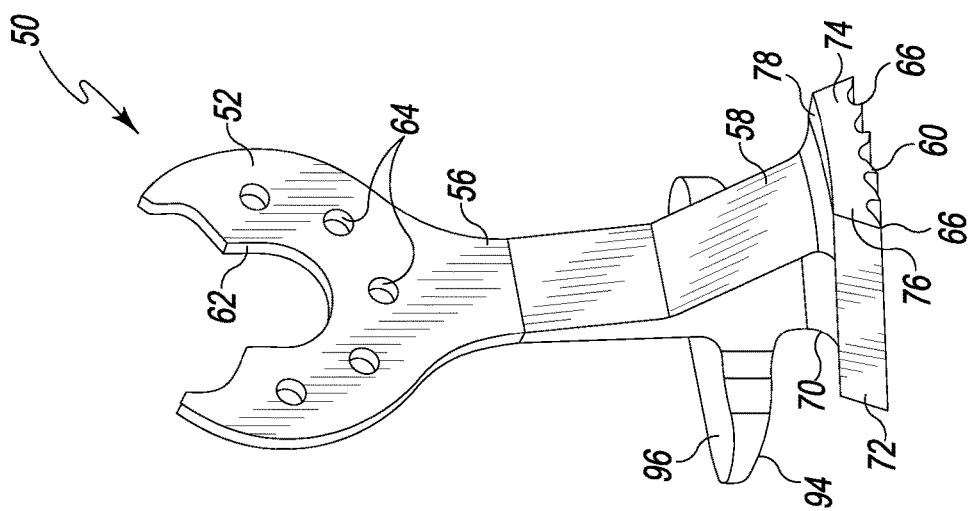

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-3, there is shown an augmented glenoid component 10. The augmented glenoid component 10 includes a body 22 having a concave surface 26 on one end thereof. The concave surface 26 of the body 22 provides a smooth bearing surface upon which a natural or prosthetic humeral head articulates. A buttress 24 extends away from the anterior medial surface 32 of the body 22 opposite the concave surface 26. The posterior medial surface 28 of the buttress 24 is substantially flat in the anterior/posterior direction and rounded (i.e., convex) in the superior/inferior direction. The anterior medial surface 32 is rounded (i.e., convex) in all directions, but may include flat portions to fit the need of a given design. A side surface 30 extends perpendicularly from the posterior medial surface 28 to the anterior medial surface 32. Alternatively, the side surface 30 may be angled relative to both surfaces 28, 32.

The augmented glenoid component 10 also includes an anchor peg 34. The anchor peg 34 extends perpendicularly from the anterior medial surface 32. The anchor peg 34 includes a tapered head 36 that functions as a lead-in to facilitate insertion into a hole drilled or otherwise formed in the glenoid surface of the patient's scapula. The glenoid component 10 also includes a plurality of stabilizing pegs 38. One of the pegs 38 extends from the anterior medial surface 32, with another of the pegs 38 extending from the posterior medial surface 28 of the buttress 24. Another of the three stabilizing pegs 38 extends from both the anterior medial surface 32 and the buttress 24—i.e., it straddles the buttress 24 and the anterior medial surface 32. Generally, the stabilizing pegs 38 are shorter than the anchor peg 34. Moreover, some of the stabilizing pegs 38 (e.g., the one extending from the anterior medial surface 32) are shorter than the others, although other configurations may be used. The stabilizing pegs 38 are received into a number of corresponding holes drilled or otherwise formed in the glenoid surface of the patient's scapula.

In the illustrative embodiment described herein, the augmented glenoid component 10 is embodied as a monolithic molded component. That is, the body 22, the anchor peg 34, and the stabilizing pegs 38 are integrally molded using a polymer such as polyethylene. One example of a suitable polyethylene is ultrahigh molecular weight polyethylene (UHMWPE). In addition to polymers, the augmented glenoid component 10 may be made from ceramic, metal, or a composite material. Examples of these materials include alumina, zirconia, and alumina/zirconia composite or composite material.

The anchor peg 34 includes a plurality of radial fins 40. The fins 40 are deformable. This allows the anchor peg 34 to fit into an anchor bore drilled in the glenoid surface of the patient's scapula, but resist removal or "pull out" of the anchor peg 34. Any number or size of radial fins 40 may be included on the anchor peg 34. In addition, although each of the fins 40 is herein described with the same sized outer diameter, it should be appreciated that other configurations are also contemplated for use. For example, the fins 40 may be provided in a tapered configuration in which the respective outer diameters of the fins 40 gradually increases from the distal end of the anchor peg 34 to the proximal end of the anchor peg 34 (i.e. the ring positioned on the distal end of the anchor peg 34 has a smaller diameter relative to the ring positioned near the proximal end of the anchor peg 34).

The fins 40 are configured to slightly deform when the anchor peg 34 is inserted into an anchor hole drilled in the patient's glenoid. This is caused when the fins 40 are advanced into the anchor hole since it is drilled to have a diameter which is slightly larger than the diameter of a shaft of the anchor peg 34, yet smaller than the outer diameter of the fins 40 thereby causing deformation of the fins 40 upon contact with the sidewalls of the drilled hole as the fins 40 are "forced" into the hole. Such deformation of the fins 40 secures the augmented glenoid component to the scapula by providing resistance to pull out of the anchor peg 34 from the drilled anchor hole much in the same way that the threads of a screw provide resistance to pull out of the screw from the material into which it is driven. In addition, over a period of time subsequent to implantation of the augmented glenoid component 10 to the patient's scapula, bone tissue or other types of tissue will grow into the spaces between the fins 40 thereby providing further resistance to pull out of the anchor peg 34 from the drilled hole.

The stabilizing pegs 38 prevent rotation or other types of movement of the augmented glenoid component 10 relative to the scapula once the glenoid component 10 has been implanted. The distal end of each of the stabilizing pegs 38 has a conical tip which functions as a "lead in" to facilitate insertion of the stabilizing pegs 38 into respective stabilizing holes drilled in the glenoid surface of the patient's scapula.

The stabilizing pegs 38 may be arranged in any orientation on the body 22 that fits the needs of a given design of an augmented glenoid component. In addition, it should be appreciated that any number of stabilizing pegs 38 may be utilized to fit the needs of a given design of an augmented glenoid component. Examples of such variations are shown in commonly-owned U.S. Pat. No. 6,699,289, the entirety of which is hereby incorporated by reference.

Referring now to FIGS. 4-9, there is shown an oscillating rasp 50 that may be used for the surgical preparation of the patient's glenoid to facilitate implantation of the complex geometry associated with the augmented glenoid component 10. The rasp 50 includes an attachment head 52 that fits into the chuck 102 of an oscillating power tool 100 (see FIG. 7). The oscillating rasp 50 also includes a cutting head 58 secured to the distal end 56 of the attachment head 52. As will be discussed in greater detail below, the geometry of the cutting head 58 corresponds with the geometry of the buttress 24 of the augmented glenoid component 10 when the oscillating rasp 50 is oscillated along a predetermined path in contact with the glenoid of the patient. The cutting head 58 of the oscillating rasp 50 includes a plurality of cutting teeth 60. When the rasp 50 is advanced into engagement with the glenoid surface of the patient's scapula with oscillating motion, the cutting teeth 60 of the oscillating rasp 50 abrade or otherwise cut the bone tissue of the scapula thereby gradually creating notch possessing the geometry (i.e., the shape) required to accept the buttress 24 of the augmented glenoid component 10. It should be appreciated that although the cutting teeth 60 are herein described as elongated, linear cutting teeth, other embodiments of cutting teeth may be used. For example, the cutting teeth 60 may be embodied as diamond knurl-type cutting teeth.

The attachment head 52 includes a keying slot 62 and a number of drive holes 64. The hub 102 of the oscillating power tool 100 includes a number of features such as detents (not shown) that are received into the keying slot 62 and drive holes 64 to couple the oscillating rasp 50 the oscillating power tool 100 (see FIG. 7). Although the attachment head 52 is herein shown with a specific exemplary mounting configuration (i.e., the configuration including the keying slot 62 and the drive holes 64), other mounting configurations are contemplated for use in the design of the attachment head 52 to allow the rasp 50 to be coupled to specific types of oscillating power tools 100. Moreover, the attachment head 52 may be embodied with a "universal" mounting configuration to allow the same rasp 50 to be coupled to multiple different oscillating power tools 100.

The cutting head 58 includes a cutting surface 66 that extends posteriorly from the longitudinal axis 68 of the oscillating rasp 50 (see FIG. 6). The cutting surface 66 of the cutting head 58 mimics the shape of the posterior medial surface 28 of the buttress 24 of the augmented glenoid component 10 when the oscillating rasp 50 is oscillated along a predetermined path in contact with the glenoid of the patient. That is, when the oscillating rasp 50 is oscillated along a predetermined path in contact with the glenoid of the patient, the cutting surface 66 produces a rasped surface that is substantially flat in the anterior/posterior direction and rounded (i.e., convex) in the superior/inferior direction. The cutting surface 66 is defined by the outer surfaces of a plurality of the cutting teeth 60. As can be seen in FIG. 6, to create such a geometry that mimics the shape of the posterior medial surface 28 of the buttress 24 of the augmented glenoid component 10, the cutting surface 66 (i.e., the outer surfaces of the cutting teeth 60) extends posteriorly away from the longitudinal axis 68 at a non-orthogonal angle. In other words, as shown in FIGS. 6 and 7, the cutting surface 66 (i.e., the outer surfaces of the cutting teeth 60) is angled upwardly when viewed front-to-back (i.e., in the anterior-to-posterior direction). This is shown geometrically in FIG. 6 where an imaginary line 80 extends posteriorly from the longitudinal axis 68 of the oscillating rasp 50 along the outer surface of each of the plurality of cutting teeth 60 (i.e., along the cutting surface 66). The imaginary line 80 intersects the longitudinal axis 68 of the oscillating rasp 50 to define an angle of intersection ($\theta$) therebetween. In an exemplary embodiment, the angle of intersection ($\theta$) is between 30°-90°. In a more specific embodiment, the angle of intersection ($\theta$) is between 30°-89° to produce a rounded surface in the superior/inferior direction. In a more specific exemplary embodiment, the angle of intersection ($\theta$) is approximately 75°. In another more specific embodiment, the angle of intersection ($\theta$) is 76.7°.

The oscillating rasp 50 may also be embodied as a tool for preparing the patient's glenoid for implantation of revision component such as a vault-type component. In particular, a revision surgery may be performed to replace a glenoid component. In such a revision surgery, the previously implanted glenoid component is surgically removed and a replacement glenoid component is implanted in the patient's glenoid. The subcondylar plate may be damaged or missing subsequent to revision surgery. Revision surgery may also result in defects, some of which may be fairly large, in the cancellous bone of the glenoid vault of the scapula. Vault-filling (i.e., vault-type) revision glenoid components have been developed that include a metal backing that extends into (i.e., "fills") the glenoid vault to replace the lost bone. A bearing component, generally made of polyethylene (e.g., UHMWPE) or other materials such as ceramics or metals, is then fixed to the implanted metal backing to create the bearing surface upon which the proximal end (e.g., a prosthetic head) of the humeral component articulates. Such a vault-type component includes a number of inclined side walls which form a wedge-shaped body. In the case of a rasp for use in implanting a vault-type revision glenoid component, the angle of intersection ($\theta$) between the imaginary line 80 and the longitudinal axis 68 of the oscillating rasp 50 is between 20°-30°.

As described above, the cutting surface 66 of the cutting head 58 mimics the shape of the posterior medial surface 28 of the buttress 24 of the augmented glenoid component 10 when the oscillating rasp 50 is oscillated along a predetermined path in contact with the glenoid of the patient. In the exemplary embodiment described herein, the throw of the oscillating tool 100 is 8°—i.e., the rasp is advanced through a 4° path in each direction from center. However, the configuration of the oscillating surgical rasp 50 allows it to accommodate any number of the different throws created by different oscillating tools 100.

As can be seen in the plan view of FIG. 8, the cutting teeth 60 of the rasp's cutting head 58 angle toward one another when viewed front-to-back (i.e., in the anterior-to-posterior direction). In particular, the cutting teeth 60 include a number of superior cutting teeth 82 and a number of inferior cutting teeth 84. The inferior cutting teeth 84 are positioned inferiorly relative to the superior cutting teeth 82. In the illustrative embodiment described herein, each of the superior cutting teeth 82 are parallel to one another, with each of the inferior cutting teeth 84 likewise being parallel to one another. The superior cutting teeth 82 and the inferior cutting teeth 84 extend posteriorly away from the longitudinal axis 68 of the oscillating rasp at an angle relative to one another so as to converge toward one another. This is shown illustratively in FIG. 8 where the anterior end 86 of a given superior cutting tooth 82 is spaced apart from the anterior end 88 of a given inferior cutting tooth 84 by a distance that is greater than the distance in which the posterior end 90 of the same superior cutting tooth 82 is spaced apart from the posterior end 92 of the same inferior cutting tooth 84. In other words, the distance between the posterior ends of a given pair of teeth 82, 84 is shorter than the distance between the same pair of teeth's anterior ends. Such an angled arrangement allows the cutting teeth 82, 84 to efficiently expel removed bone tissue during operation of the oscillating rasp 50.

The rasp's cutting head 58 also has a number of non-cutting surfaces. In particular, a substantially flat, smooth anterior sidewall 70 extends upwardly from the anterior end 72 of the cutting head 58. As shown in FIG. 6, the anterior sidewall 70 is devoid of cutting teeth. A posterior sidewall 74 extends upwardly from the posterior end 76 of the cutting surface 66 to a backside surface 78 of the cutting head 58. Like the anterior side wall 70, the posterior sidewall 74 and the backside surface 78 are devoid of cutting teeth.

As can be seen in FIG. 7, the cutting surface 66 of the oscillating surgical rasp 50 has a radius of curvature $R_1$. As can be seen in FIG. 7, the origin of the cutting surface's radius of curvature is the center of the keying slot 62. This represents the center of oscillation when the rasp 50 is operated. As described above, the posterior medial surface 28 of the buttress 24 of the augmented glenoid component 10 is rounded (i.e., convex) in the superior/inferior direction. As can be seen in FIG. 2, the rounded surface of the posterior medial surface 28 of the buttress 24 has a radius of curvature $R_2$. The oscillating rasp 50 is embodied such that the radius of curvature $R_1$ of its cutting surface 66 closely mimics the radius of curvature $R_2$ of the posterior medial surface 28 of the buttress 24 of the augmented glenoid component 10. In one exemplary embodiment, the length of the radius of curvature $R_1$ of the rasp's cutting surface 66 is ±5 mm of the length of the radius of curvature $R_2$ of the posterior medial surface 28 of the buttress 24 of the augmented glenoid component 10. In a more specific exemplary embodiment, the length of the radius of curvature $R_1$ of the rasp's cutting surface 66 is ±3 mm of the length of the radius of curvature $R_2$ of the posterior medial surface 28 of the buttress 24 of the augmented glenoid component 10. In an even more specific exemplary embodiment, the length of the radius of curvature $R_1$ of the rasp's cutting surface 66 is equal to the length of the radius of curvature $R_2$ of the posterior medial surface 28 of the buttress 24 of the augmented glenoid component 10. In the illustrative embodiment described herein, both the length of the radius of curvature $R_1$ of the rasp's cutting surface 66 and the length of the radius of curvature $R_2$ of the posterior medial surface 28 of the buttress 24 of the augmented glenoid component 10 are 32.97 mm.

The cutting head 58 of the oscillating rasp 50 also includes a depth stop 96. The depth stop 96 extends in the direction opposite to the cutting surface 66. In other words, the depth stop 96 extends anteriorly from the longitudinal axis 68 of the oscillating rasp 50. As will be described below in greater detail, the depth stop 96 bottoms out on a rasp guide 110 secured to the reamed surface of the patient's glenoid to ensure the posterior glenoid surface is prepared to the desired depth relative to the anterior glenoid surface. In other words, the depth stop 96 creates a spatial relationship (i.e., a depth) between the surgically-prepared anterior and posterior glenoid surfaces which matches the distance between the posterior medial surface 28 of the glenoid component's buttress 24 and its anterior medial surface 32. Such a distance is defined by the height of the side surface 30 that extends perpendicularly from the posterior medial surface 28 of the buttress 24 to the anterior medial surface 32 of the augmented glenoid component 10 (see FIGS. 1-3).

The depth stop 96 may be embodied as a number of different structures. For example, the depth stop 96 may be embodied as one or more tabs, bars, flanges, other similar structures configured to bottom out on the rasp guide 110 secured to the anterior surface of the patient's glenoid to prevent further penetration of the cutting head 58 into the posterior surface of the patient's glenoid. In the exemplary embodiment described herein, the depth stop 96 is embodied as a generally oval-shaped bar that has its edge secured to the anterior sidewall 70 of the rasp's cutting head 58.

In the illustrative embodiment described herein, the oscillating surgical rasp 50 is embodied as a monolithic component. Hence, the attachment head 52 is integrally formed with the cutting head 58. The oscillating surgical rasp 50 may be constructed from a medical-grade metal such as stainless steel, cobalt chrome, or titanium, although other metals or alloys may be used. Moreover, in some embodiments, rigid polymers such as polyaryetheretherketone (PEEK) may also be used.

Referring now to FIGS. 10-14, there is shown a rasp guide 110 for use along with the oscillating rasp 50 in a surgical procedure to implant the augmented glenoid component 10. The rasp guide 110 includes a body 122 having a concave guide surface 126 on one end thereof. The concave guide surface 126 of the body 122 provides a smooth guide surface upon which depth stop 96 bottoms out and thereafter articulates during operation of the oscillating surgical rasp 50. An anchor surface 132 is formed in the side of the body 122 opposite the concave surface 126. The anchor surface 132 is rounded (i.e., convex) and configured to be secured to the glenoid of the patient.

The rasp guide 110 also includes an anchor peg 134. The anchor peg 134 extends perpendicularly from the anchor surface 132. The anchor peg 134 includes a tapered head 136 that functions as a lead-in to facilitate insertion into a hole drilled or otherwise formed in the glenoid surface of the patient's scapula. In the illustrative embodiment described herein, the anchor peg 134 of the rasp guide 110 shares a common configuration (e.g., length and diameter) with the anchor peg 34 of the augmented glenoid component 10. The rasp guide 110 also includes a number of pointed anchoring pins 138. The anchoring pins 138 extend perpendicularly away from the anchor surface 132 of the rasp guide 110. The anchoring pins 138 may be driven into the glenoid of the patient to stabilize the rasp guide 110 (e.g., prevent it from rotating about the anchor peg 134). As can be seen in FIGS. 13 and 14, a hole 140 extends through the body 122 if the rasp guide 110. A separate anchoring pin (not shown) can be inserted through the hole 140 and driven into the glenoid of the patient to further stabilize the rasp guide 110.

When the rasp guide 110 is secured to the patient's glenoid, the posterior edge 142 of the rasp guide 110 defines a vertical boundary between the anterior and posterior portions of the glenoid. As such, the rasp guide 110 protects the prepared anterior surface and the center hole (i.e., the hole into which the anchor peg 34 of the augmented glenoid component 10 is inserted). As will be discussed below in greater detail, during rasping with the oscillating rasp 50, the cutting head 58 is prevented from cutting anteriorly of the edge 142 of the rasp guide 110 thereby creating a wall of bone in the center of the glenoid that serves as the perpendicular step between the anterior and posterior halves of the medial surface of the augmented glenoid component 10—i.e., a surgically prepared surface that corresponds with the side surface 30 of the augmented glenoid component 10.

As can be seen in FIG. 12, the guide surface 126 of the rasp guide 110 has a radius of curvature $R_3$. As described above and as can be seen in FIG. 2, the rounded surface of the posterior medial surface 28 of the buttress 24 has a radius of curvature $R_2$. The cutting guide 11 is embodied such that the radius of curvature $R_3$ of its guide surface 126 closely mimics the radius of curvature $R_2$ of the posterior medial surface 28 of the buttress 24 of the augmented glenoid component 10. In one exemplary embodiment, the length of the radius of curvature $R_3$ of the guide's guide surface 126 is ±5 mm of the length of the radius of curvature $R_2$ of the posterior medial surface 28 of the buttress 24 of the augmented glenoid component 10. In a more specific exemplary embodiment, the length of the radius of curvature $R_3$ of the guide's guide surface 126 is ±3 mm of the length of the radius of curvature $R_2$ of the posterior medial surface 28 of the buttress 24 of the augmented glenoid component 10. In an even more specific exemplary embodiment, the length of the radius of curvature $R_3$ of the guide's guide surface 126 is equal to the length of the radius of curvature $R_2$ of the posterior medial surface 28 of the buttress 24 of the augmented glenoid component 10. In the illustrative embodiment described herein, both the length of the radius of curvature $R_3$ of the guide's guide surface 126 and the length of the radius of curvature $R_2$ of the posterior medial surface 28 of the buttress 24 of the augmented glenoid component 10 are 32.97 mm.

In the illustrative embodiment described herein, the rasp guide 110 is embodied as a monolithic component. Hence, the body 122 is integrally formed with the anchor peg 134.

The rasp guide 110 may be constructed from a medical-grade metal such as stainless steel, cobalt chrome, or titanium, although other metals or alloys may be used. Moreover, in some embodiments, rigid polymers such as polyaryetheretherketone (PEEK) may also be used.

Referring now to FIGS. 15-20, there is shown a surgical procedure in which the oscillating rasp 50 is used to surgically prepare the patient's glenoid 184 for implantation of the augmented glenoid component 10. The surgical procedure begins with preoperative planning in which, amongst other things, a thin cut (1 mm) axial CT scan with the gantry positioned perpendicular to the plane of the glenoid and plane of the scapula is obtained. A single axial slice just below the mid-equator of the glenoid is obtained for measurement of glenoid version. Correction of retroversion may then be individualized to the patient. With the preoperative planning complete, the patient's soft tissue is dissected and retracted in order to allow access to the glenoid. Full (i.e., 360°) exposure of the bony glenoid is typically achieved.

Figure 15:
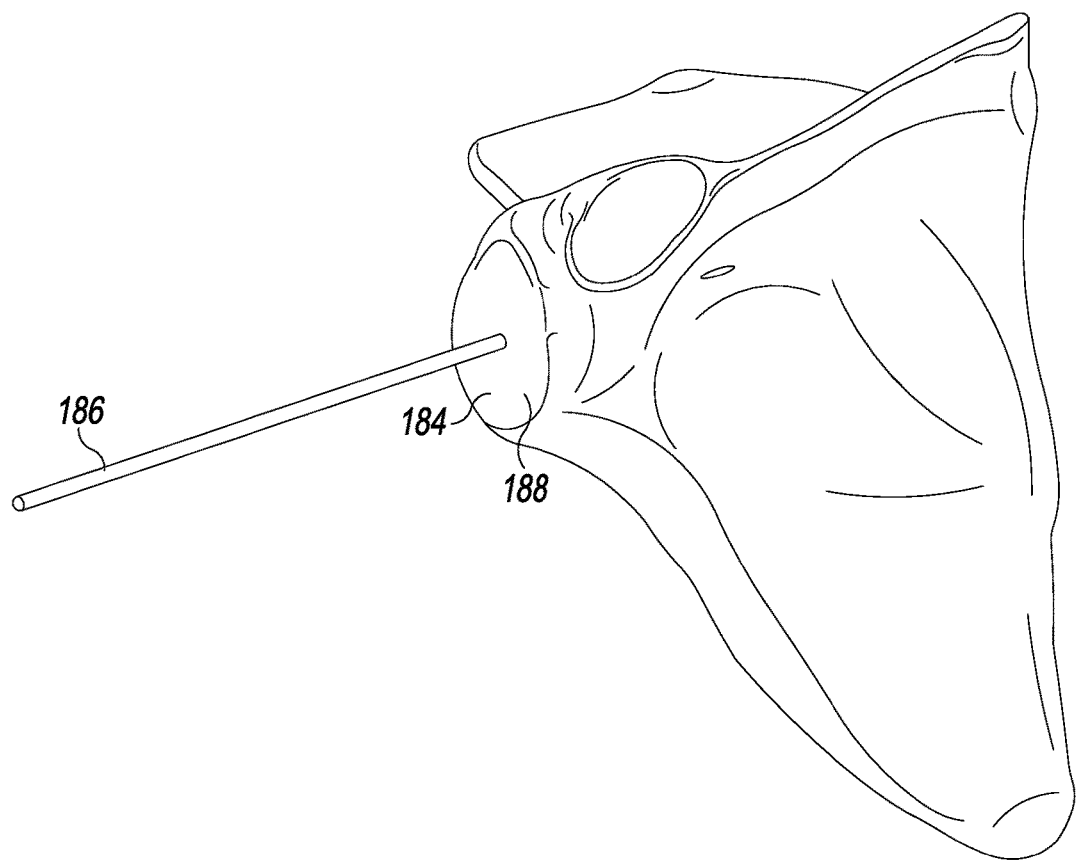
FIG. 15 is an anterior perspective view showing a guide pin inserted in the glenoid of a patient during a surgical procedure to implant the augmented glenoid component of FIGS. 1-3.

As shown in FIG. 15, a guide pin 186 is then inserted in the center of the glenoid 184 in an orientation that will allow for the desired amount of retroversion correction. This can be accomplished using one of a number of different pin placement devices. The guide pin 186 may be scored in locations along its length to allow for controlled breakage to adjust the length of the pin 186 subsequent to being inserted. Specifically, at any point in the procedure, the guide pin 186 can be shortened to a more desirable length by placing a handle just above a score mark and a needle driver just below the same score mark and bending the pin 186 at the score mark. In the illustrative procedure described herein, two to three inches of the pin 186 protrude laterally from the glenoid.

A sizer pin guide (not shown) may then be placed over the guide pin 186. The sizer pin guide is used determine the optimal size augmented glenoid component for the patient's glenoid. Typically, a desired size of an augmented glenoid component covers as much of the glenoid surface as possible without overhanging the periphery of the bone surface.

Figure 16:
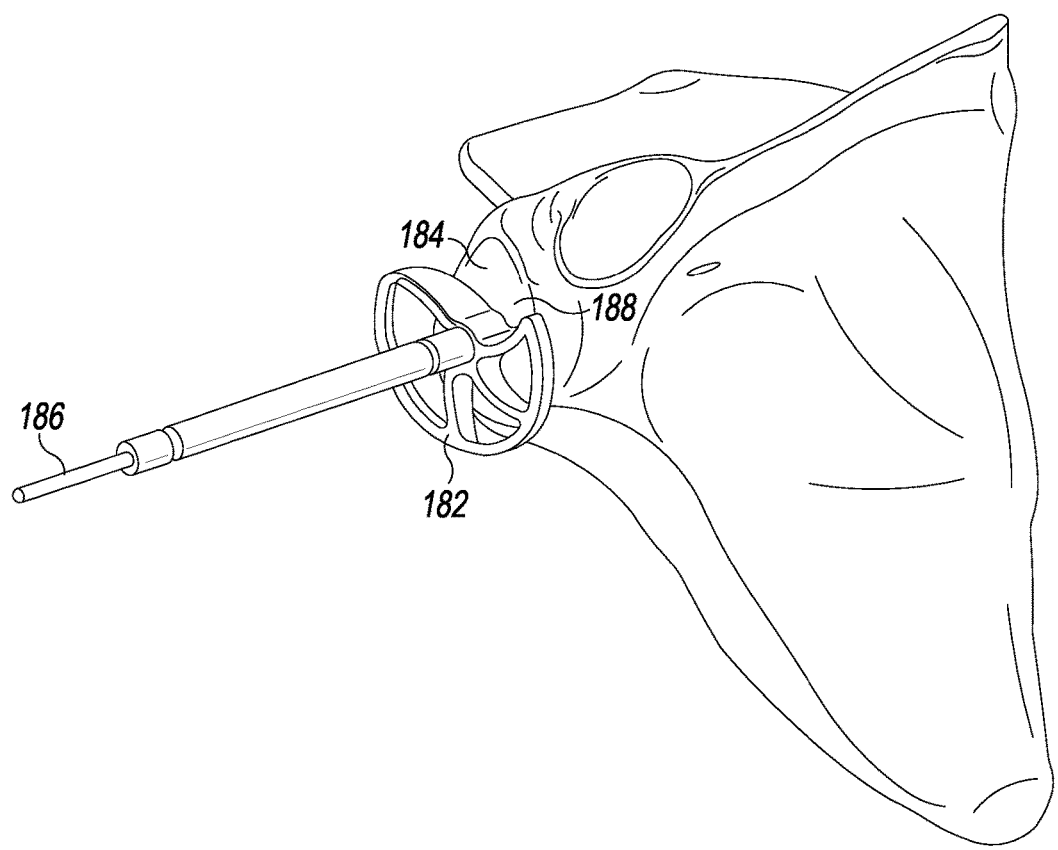
FIG. 16 is a view similar to FIG. 15 showing reamer being used to ream the patient's glenoid.
Figure 17:
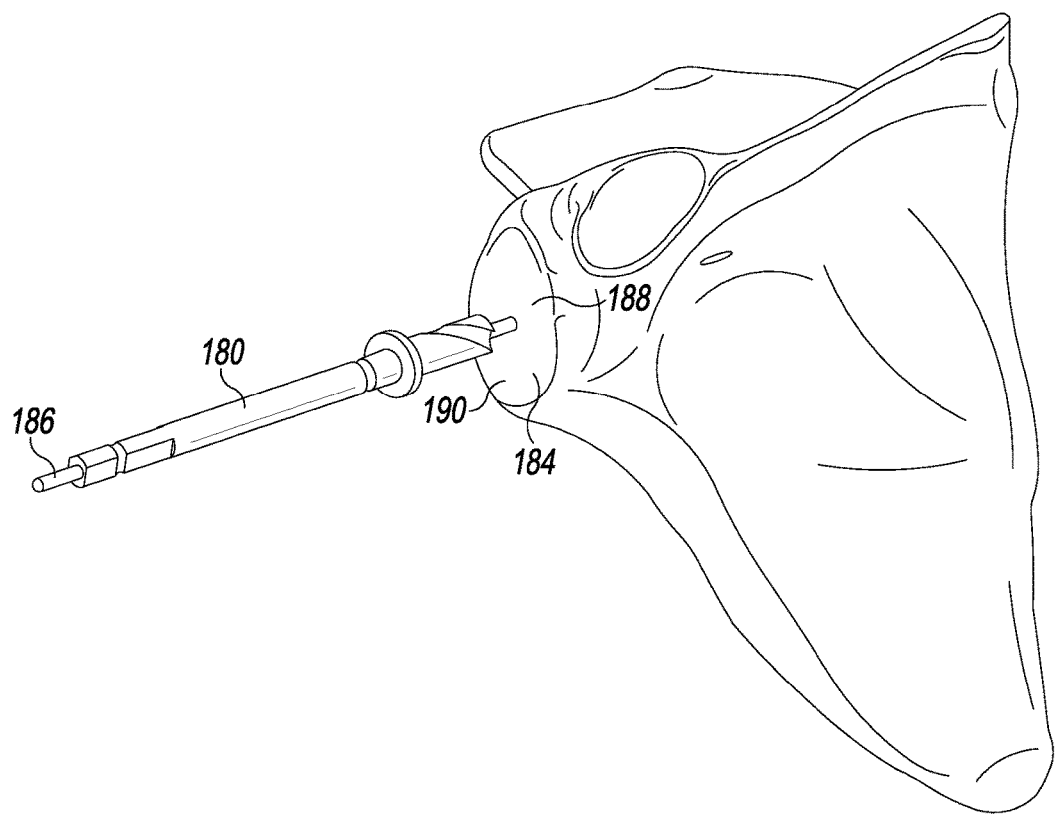
FIG. 17 is a view similar to FIG. 15 showing a drill being used to drill the anchor hole into the patient's glenoid.

The anterior surface 188 of the patient's glenoid 184 is then reamed in a typical manner. In particular, as shown in FIG. 16, a spherical reamer 182 is used over the guide pin 186 to ream the anterior surface 188 of the glenoid and create an even, concave surface from the superior edge of the glenoid 184 (i.e., 12 o'clock) to the inferior edge of the glenoid 184 (i.e., 6 o'clock). This reamed surface 190 is the final surgically-prepared surface that contacts the anterior medial surface 32 of the augmented glenoid component 10 when it is implanted. It should be appreciated that if the spherical reamer 182 used is smaller than the superior/inferior dimension of the augmented glenoid component 10, a small amount of bone on the superior and/or inferior aspects of the anterior glenoid will remain. This remaining bone may be removed with a peripheral reamer (not shown). A hand burr (not shown) may be alternatively used to remove the remaining bone. The reamed surface 190 of the patient's anterior glenoid 184 is shown in FIG. 17.

A depth gauge (not shown) may then be placed over the guide pin 186. The contact and conformity between the back surface of the depth gauge and the prepared anterior glenoid surface 190 is the determined. Further preparation of the bone may then be performed if the contact and conformity is not to the surgeon's satisfaction. The maximum depth of the posterior glenoid defect is measured by inserting a depth probe (not shown) through the depth gauge. In one illustrative instrument, three holes in the posterior half of the depth gauge are provided so that three different locations and their respective depths can be evaluated. In most cases the greatest depth of the defect is on the posterior, inferior quadrant of the glenoid. Such an evaluation allows for implant selection (i.e., selection of a particularly sized augmented glenoid component 10). For example, if the maximum depth is 3 mm or less, an augmented glenoid component 10 with a 3 mm augment (i.e., a 3 mm thick buttress 24) is needed. If the depth measured is between 3 mm and 5 mm, an augmented glenoid component 10 with a 5 mm augment is needed. If the depth measured is between 5 mm and 7 mm, an augmented glenoid component 10 with a 7 mm augment is needed. In the illustrative procedure described herein, if the depth measured is more than 7 mm, additional bone may need to be removed from the anterior surface 188 of the patient's glenoid 184. In this illustrative case, the amount of additional bone to be removed is equal to the maximum defect minus 7 mm.

The appropriate size posterior preparation guide (not shown) is then placed over the guide pin 186 so that it firmly and concentrically contacts the prepared anterior glenoid surface 190. The posterior window in the guide defines the boundaries of the posterior surface 194 of the glenoid 184 to be prepared to accept the buttress 24 of the augmented glenoid component 10, and it can be used as a template for marking these boundaries with either a sterile pen, saw blade, or a bovie.

Once the boundaries of the buttress 24 have been marked, the posterior glenoid is surgically prepared. At the outset, as shown in FIG. 17, a cannulated center drill 180 of the appropriate length based on the step height of the buttress 24 of the selected augmented glenoid component 10 is inserted over the guide pin 186. The drill is then used to prepare (i.e., drill) the glenoid 184 to accept the anchor peg 34 of the augmented glenoid component 10. The drill 180 is advanced until it bottoms out on the reamed anterior surface 190 of the glenoid 184. Once the center hole 178 for the anchor peg 34 has been drilled, a pin puller or other instrument (not shown) is used to grasp and remove the guide pin 186.

Figure 18:
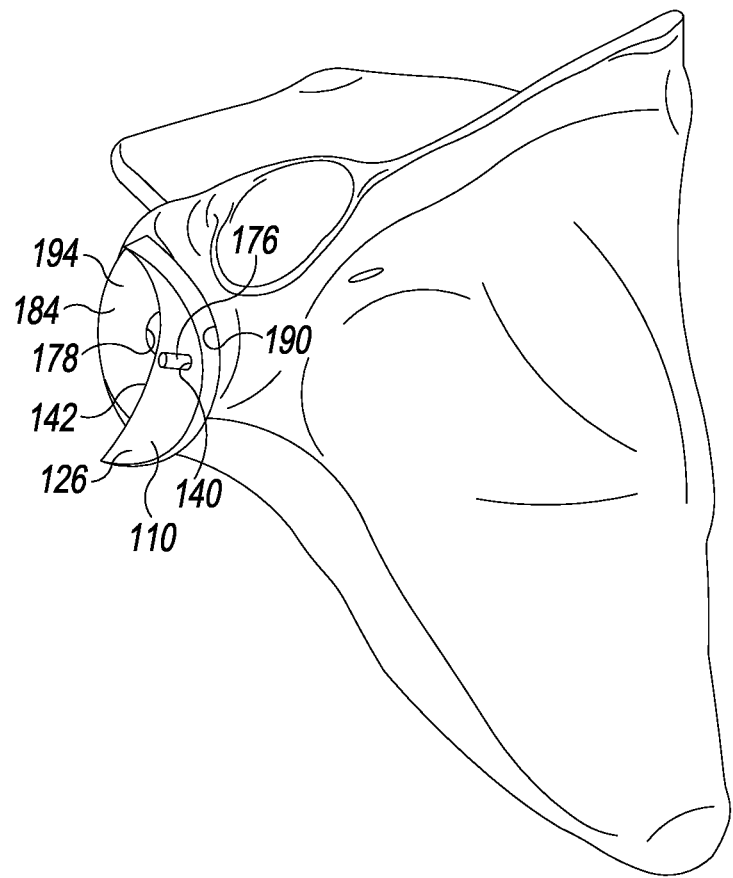
FIG. 18 is a view similar to FIG. 15 showing the rasp guide secured to the patient's glenoid.

As shown in FIG. 18, the appropriate sized rasp guide 110 is then secured to the reamed anterior surface 190 of the glenoid 184. To do so, the tapered head 136 of the rasp guide's anchor peg 134 is inserted into the center hole 178 drilled in the reamed anterior surface 190 of the glenoid 184. The rasp guide 110 may then be tapped with a surgical mallet (not shown) or other instrument to drive the anchoring pins 138 of the rasp guide 110 into the glenoid 184 of the patient to stabilize the rasp guide 110 (e.g., prevent it from rotating about the anchor peg 134). Optionally, an additional anchoring pin 176 can be inserted through the hole 140 and driven into the glenoid 184 of the patient to further stabilize the rasp guide 110.

As can be seen in FIG. 18, when the rasp guide 110 is secured to the patient's glenoid 184, the posterior edge 142 of the rasp guide 110 defines a vertical boundary between the reamed anterior surface 190 and the posterior surface 194 of the glenoid 184 that is to be rasped. As such, the rasp guide 110 protects the prepared anterior surface 190 and the center hole 178. In the illustrative embodiment described herein, the rasp guide is centered in the anterior/posterior direction. As such, the vertical boundary created by the guide's posterior 142 divides the glenoid 184 into two equally sized halves in the anterior/posterior direction. As will be discussed below in regard to FIG. 19, during rasping with the oscillating rasp 50, the cutting head 58 is prevented from cutting anteriorly of the edge 142 of the rasp guide 110 thereby creating a wall of bone in the center of the glenoid 184 that serves as the perpendicular step between the anterior and posterior halves of the medial surface of the augmented glenoid component 10—i.e., a surgically prepared surface that corresponds with the side surface 30 of the augmented glenoid component 10.

Figure 19:
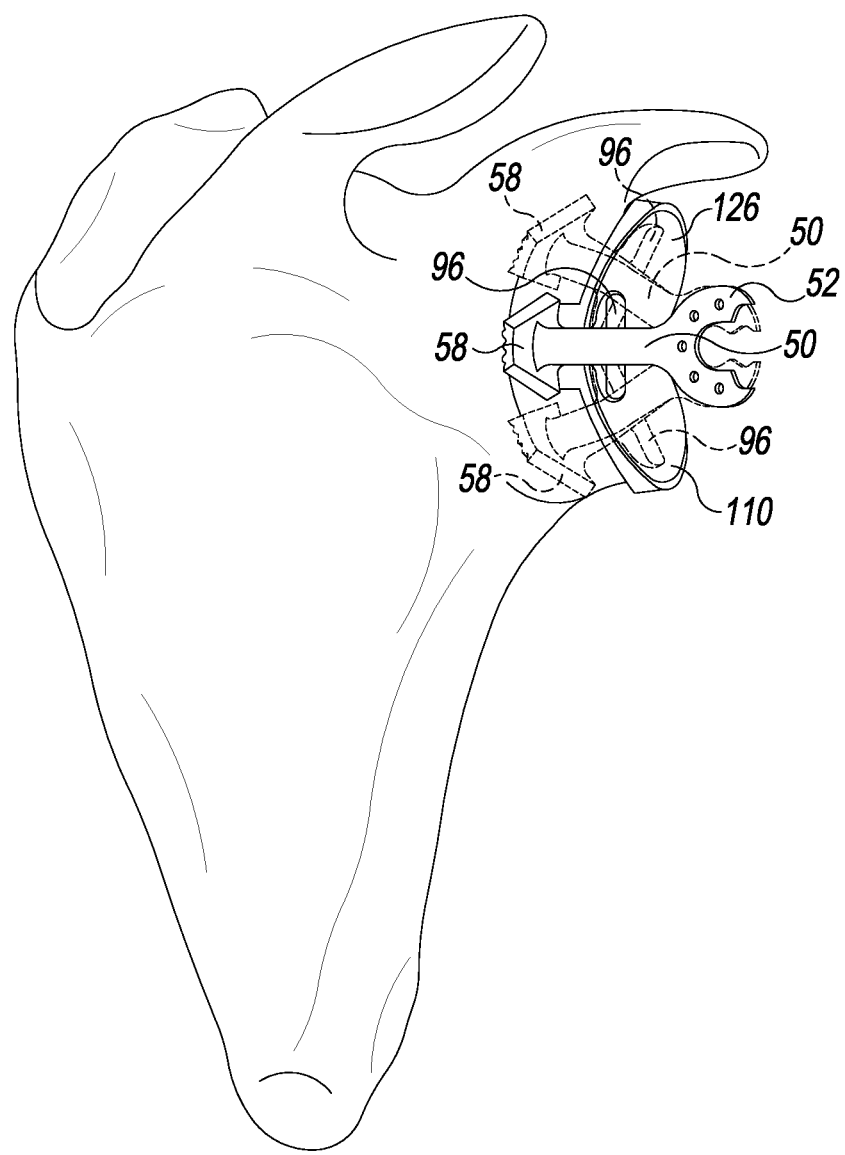
FIG. 19 is a posterior perspective view showing the oscillating rasp of FIGS. 4-6 during rasping the patient's glenoid.
Figure 20:
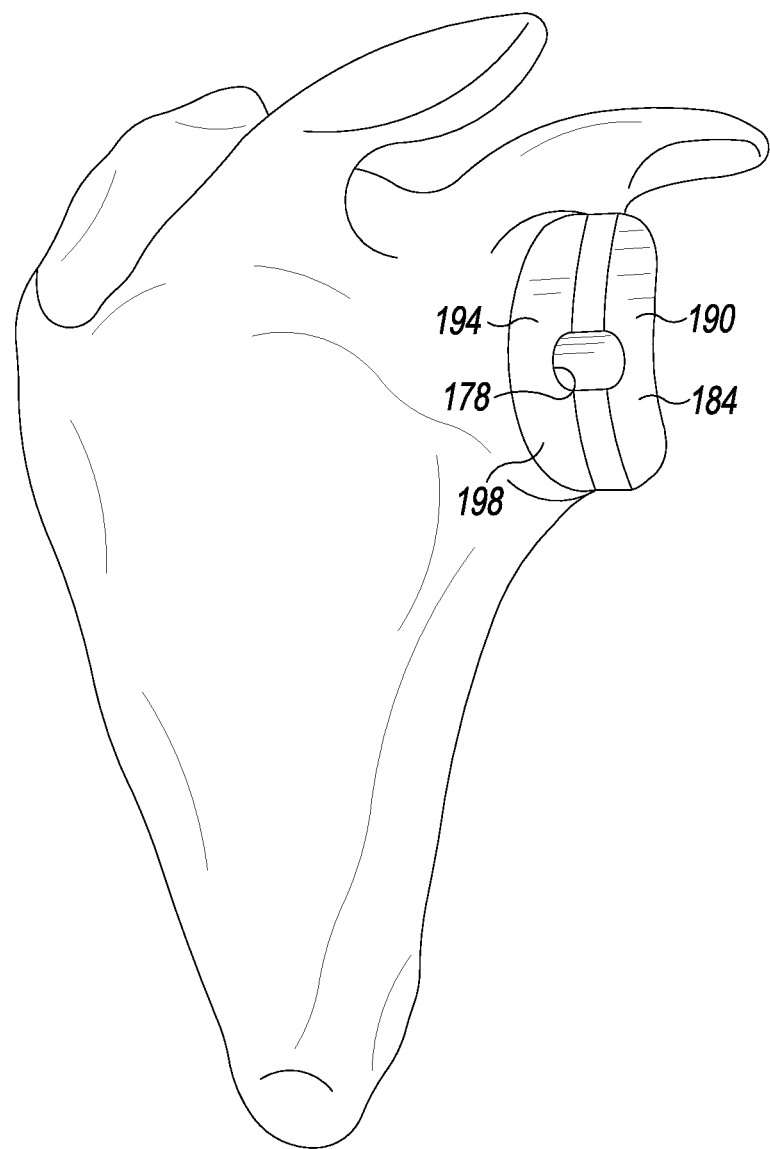
FIG. 20 is a view similar to FIG. 19 showing the patient's glenoid after it has been surgically prepared with the oscillating rasp of FIGS. 4 and 5.

An oscillating rasp 50 sized to match the buttress 24 of the selected augmented glenoid component 10 is then obtained from a number of differently-sized rasps 50 and used to complete the posterior preparation. The attachment head 52 of the selected oscillating rasp 50 is then secured within the chuck 102 of the oscillating power tool 100 (see FIG. 7). Once chucked, the rasp 50 is advanced into contact with the posterior portion of the glenoid 184. As shown in FIG. 19, the surgeon then activates the oscillating power tool 100 and advances the cutting surface 66 of the cutting head 58 into contact with the posterior surface 194 of the glenoid 184. As the rasp 50 is advanced inwardly toward the patient's glenoid 184, the oscillating motion of the rasp 50 abrades the bone and continues to remove bone until the leading surface 94 of the depth stop 96 (see FIGS. 4-7) bottoms out on the concave guide surface 126 of the rasp guide 110. The surgeon continues to oscillate the rasp 50 with the depth stop 96 riding on the concave guide surface 126 thereby using the rasp guide 110 as a preparation guide. This ensures the posterior glenoid surface 194 is prepared to the desired depth relative to the anterior glenoid surface 190. In other words, the depth stop 96 creates a spatial relationship (i.e., a depth) between the surgically-prepared anterior surface 190 and the posterior glenoid surface 194 which matches the distance between the posterior medial surface 28 of the glenoid component's buttress 24 and its anterior medial surface 32. Such a distance is defined by the height of the side surface 30 that extends perpendicularly from the posterior medial surface 28 of the buttress to the anterior medial surface 32 of the augmented glenoid component 10 (see FIGS. 1-3). When the depth stop 96 of the rasp 50 contacts the concave guide surface 126 thereby using the rasp guide 110 in such a manner, the posterior preparation of the glenoid 184 is complete—i.e., the rasped posterior glenoid surface 198 has been completed (see FIG. 20).

It should be appreciated that in lieu of completing the rasped posterior glenoid surface 198 with a single rasp 50, a number of differently-sized rasps 50 may be used. In particular, a number of progressively larger-sized rasps 50 may be used to produce the desired final size. For example, initial rasping may be performed with a rasp 50 having a relatively small cutting head 58. Thereafter, one or more additional rasps 50 having progressively larger cutting heads 58 may be used to perform subsequent rasping to form a larger cavity of the desired final size.

A bone preparation assessor (not shown), which is sized to mimic the medial surfaces of the selected augmented glenoid component 10, is then used to determine whether the anterior reaming and posterior rasping of the bony surfaces was sufficient to accommodate the selected augmented glenoid component 10. The bone preparation assessor generally makes full and concentric contact with the prepared glenoid surfaces. If high spots on the bone are preventing the bone preparation assessor from seating completely, an impactor, tamp, or other instrument may be used to make the prepared glenoid surfaces more conforming. The fit of the bone preparation assessor may then be assessed again.

A peripheral drill guide (not shown) specific to the selected augmented glenoid component 10 is then inserted into the drilled center hole. The holes for the stabilizing pegs 38 are then drilled with the assistance of the drill guide.

An implant trial (not shown) is placed into the prepared glenoid 184, and its fit is assessed. Full and concentric contact between the medial side of the trial and the prepared surfaces of the bone is generally desired. If this is not the case, some or all of the prior bone preparation steps may be repeated. If the fit is adequate, the trial is removed.

Finely morselized bone retrieved during the glenoid preparation is used to create a "bone paste." This bone paste is interposed between the fins 40 of the anchor peg 34 of the augmented glenoid component 10 to facilitate tissue integration. Bone cement, such as PMMA-based bone cement, is placed in the peripheral holes (i.e., the holes for the stabilizing pegs 38) of the prepared glenoid 184 and pressurized using a fingertip. The augmented glenoid component 10 is then inserted, and a glenoid impactor (not shown) is used to seat the component 10 until there is complete contact with the perimeter of the glenoid 184. Pressure on the implanted component 10 is maintained until the cement has hardened.

It should be appreciated that modifications to the above-described surgical procedure are contemplated. For example, some surgeons may prefer to perform the rasping procedure "free hand" without the use of the rasp guide 110. In such a case, once the boundaries of the buttress 24 have been marked, the surgeon may use a saw blade or other surgical tool to create a channel in the midline of the patient's glenoid 184 in the superior/inferior direction. The depth of such a channel is guided by the etch marks on the saw blade. For example, for a 3 mm augment, the saw blade should be advanced until the 3 mm etch mark is at the same level as the surface of the glenoid 184. This creates a wall of bone in the center of the glenoid 184 that serves as the perpendicular step between the anterior and posterior halves of the medial surface of the augmented glenoid component 10—i.e., a surgically prepared surface that corresponds with the side surface 30 of the augmented glenoid component 10.

The surgeon may then rasp the posterior glenoid surface 194 using the surgically-prepared anterior surface 190 as a guide surface. Namely, the surgeon may rasp the posterior glenoid surface 194 with the depth stop 96 riding on the surgically-prepared anterior surface 190 thereby using the reamed anterior glenoid surface 190 as a guide surface.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, the oscillating rasp 50 described herein may be used to surgically prepare the bony anatomy for other types of arthroplasty. For instance, the oscillating rasp 50, with or without some modification thereto, may be used in a hip procedure or other type of joint procedure. Moreover, the oscillating rasp 50 may be used to prepare the other surfaces of the glenoid, such as the anterior glenoid surface. The oscillating rasp 50 may also be used in a bone grafting procedure for shaping the glenoid surface.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An oscillating surgical rasp for use in surgical preparation of a glenoid of a patient prior to implantation of an augmented glenoid prosthesis, the oscillating surgical rasp comprising:
    an attachment head including a body extending along a longitudinal axis from a first end configured to be secured in a chuck of an oscillating tool to a second end, and
    a cutting head secured to the second end of the attachment head, the cutting head comprising a cutting surface extending posteriorly away from the longitudinal axis of the oscillating surgical rasp at a non-orthogonal angle, the cutting surface having a plurality of cutting teeth arranged in a geometry that, when oscillated along a predetermined path in contact with the glenoid of the patient, corresponds with a geometry of the augmented glenoid prosthesis,
    wherein the first end of the body of the attachment head defines an axis of oscillation that extends orthogonal to the longitudinal axis of the oscillating surgical rasp.

2. The oscillating surgical rasp of claim 1, wherein the cutting head further comprises a depth stop extending anteriorly from the longitudinal axis of the oscillating surgical rasp.

3. The oscillating surgical rasp of claim 1, wherein:
    an imaginary line extends posteriorly from the longitudinal axis of the oscillating surgical rasp along an outer surface of each of the plurality of cutting teeth,
    the imaginary line intersects the longitudinal axis of the oscillating surgical rasp to define an angle of intersection therebetween, and
    the angle of intersection is between 30°-90°.

4. The oscillating surgical rasp of claim 1, wherein:
    the plurality of cutting teeth of the cutting head comprises a superior cutting tooth and an inferior cutting tooth that is positioned inferiorly relative to the superior cutting tooth,
    an anterior end of the superior cutting tooth is spaced apart from an anterior end of the inferior cutting tooth by a first distance, and
    a posterior end of the superior cutting tooth is spaced apart from a posterior end of the inferior cutting tooth by a second distance that is shorter than the first distance.

5. The oscillating surgical rasp of claim 1, wherein:
    the plurality of cutting teeth of the cutting head comprises a number of superior cutting teeth and a number of inferior cutting teeth that are positioned inferiorly relative to the number of superior cutting teeth,
    the number of superior cutting teeth are arranged parallel to one another and the number of inferior cutting teeth are arranged parallel to one another, and
    the number of superior cutting teeth and the number of inferior cutting teeth extend posteriorly from the longitudinal axis of the surgical rasp at an angle relative to one another so as to converge toward one another.

6. The oscillating surgical rasp of claim 1, wherein the plurality of cutting teeth of the cutting head are arranged in a geometry that, when oscillated along a predetermined path in contact with the glenoid of the patient, corresponds with the geometry of a posterior buttress of the augmented glenoid prosthesis.

7. The oscillating surgical rasp of claim 1, wherein the length of the radius of curvature of the cutting surface of the cutting head is ±5 mm of the length of the radius of curvature of a rounded posterior medial surface of a buttress of the augmented glenoid component.

8. The oscillating surgical rasp of claim 1, wherein the length of the radius of curvature of the cutting surface of the cutting head is ±3 mm of the length of the radius of curvature of a rounded posterior medial surface of a buttress of the augmented glenoid component.

9. The oscillating surgical rasp of claim 1, wherein the length of the radius of curvature of the cutting surface of the cutting head is equal to the length of the radius of curvature of a rounded posterior medial surface of a buttress of the augmented glenoid component.

10. The oscillating surgical rasp of claim 1, wherein each cutting tooth of plurality of cutting teeth extends from an anterior end of the cutting tooth, posteriorly from the longitudinal axis, to a posterior end of the cutting tooth, and
    wherein the anterior end of each cutting tooth is positioned proximal of the posterior end of the same cutting tooth.

* * * * *